(12) United States Patent
Pribitkin

(10) Patent No.: US 10,022,506 B2
(45) Date of Patent: Jul. 17, 2018

(54) HYPODERMIC INJECTION DEVICE INCORPORATED IN A CASE FOR A PORTABLE ELECTRONIC DEVICE

(71) Applicant: Thomas Jefferson University, Philadelphia, PA (US)

(72) Inventor: Edmund Pribitkin, Blue Bell, PA (US)

(73) Assignee: THOMAS JEFFERSON UNIVERSITY, Philadelphia, PA (US)

( * ) Notice: Subject to any disclaimer, the term of this patent is extended or adjusted under 35 U.S.C. 154(b) by 882 days.

(21) Appl. No.: 14/391,644

(22) PCT Filed: Apr. 8, 2013

(86) PCT No.: PCT/US2013/035546
§ 371 (c)(1),
(2) Date: Oct. 9, 2014

(87) PCT Pub. No.: WO2013/154954
PCT Pub. Date: Oct. 17, 2013

(65) Prior Publication Data
US 2015/0080806 A1    Mar. 19, 2015

Related U.S. Application Data

(60) Provisional application No. 61/622,681, filed on Apr. 11, 2012.

(51) Int. Cl.
*A61M 5/32* (2006.01)
*A61M 5/20* (2006.01)
(Continued)

(52) U.S. Cl.
CPC ............ *A61M 5/3287* (2013.01); *A61M 5/20* (2013.01); *A61M 5/2033* (2013.01);
(Continued)

(58) Field of Classification Search
CPC .......... A61M 5/20; A61M 5/32; A61M 5/152; A61M 5/315; A61M 5/2033; A61M 5/326;
(Continued)

(56) References Cited

U.S. PATENT DOCUMENTS

| | | |
|---|---|---|
| 5,176,643 A | 1/1993 | Kramer et al. |
| 5,658,259 A | 8/1997 | Pearson et al. |

(Continued)

FOREIGN PATENT DOCUMENTS

WO    WO-2010/049239    5/2010

OTHER PUBLICATIONS

International Search Report for corresponding International Application No. PCT/US2013/035546, dated Jul. 26, 2013, 4 pages.
(Continued)

*Primary Examiner* — Kevin C Sirmons
*Assistant Examiner* — Tiffany Legette-Thompson
(74) *Attorney, Agent, or Firm* — Cozen O'Connor

(57) ABSTRACT

A hypodermic injection device configured to be attached to a portable electronic device is disclosed herein. The hypodermic injection device can be an auto-injector for delivering a dose of an injectable medicament. The injection device can include a durable barrier providing a sheath over an injectable cannula to maintain sterility of an injectable cannula that delivers the medicament. The injection device can also include tamper proof features such as by requiring that deployment of the device only be possible after completing two mechanical manipulations so as to prevent accidental discharge of the injection device. By incorporating the injection device within a case for a portable electronic device, the injection device is readily available to those that rely on auto-injectors to provide emergency (Continued)

therapeutic treatment, and is much less likely to be forgotten or left behind by a user than a typical auto-injector.

21 Claims, 7 Drawing Sheets

(51) Int. Cl.
*G06F 1/16* (2006.01)
*H04M 1/21* (2006.01)
*A61M 5/315* (2006.01)
*A61M 5/31* (2006.01)
*A61M 5/00* (2006.01)
*H04M 1/02* (2006.01)
*H04M 1/18* (2006.01)

(52) U.S. Cl.
CPC ...... *A61M 5/3158* (2013.01); *A61M 5/31501* (2013.01); *A61M 5/3245* (2013.01); *G06F 1/1656* (2013.01); *H04M 1/21* (2013.01); *A61M 5/002* (2013.01); *A61M 5/326* (2013.01); *A61M 2005/2013* (2013.01); *A61M 2005/2026* (2013.01); *A61M 2005/2073* (2013.01); *A61M 2005/314* (2013.01); *A61M 2005/3142* (2013.01); *A61M 2209/08* (2013.01); *H04M 1/0256* (2013.01); *H04M 1/185* (2013.01)

(58) Field of Classification Search
CPC .............. A61M 5/3287; A61M 5/3158; A61M 5/3245; A61M 5/31501; A61M 2005/208; A61M 2005/2013
USPC .................................................. 604/189, 198
See application file for complete search history.

(56) References Cited

U.S. PATENT DOCUMENTS

| | | |
|---|---|---|
| 6,102,896 A | 8/2000 | Roser |
| 2003/0212362 A1 | 11/2003 | Roser |
| 2009/0270804 A1* | 10/2009 | Mesa .................. A61M 5/2033 604/111 |
| 2010/0160894 A1* | 6/2010 | Julian ................. A61M 5/2033 604/506 |
| 2010/0234811 A1* | 9/2010 | Schubert ............... A61M 5/326 604/198 |
| 2010/0298768 A1* | 11/2010 | Halili, Jr. .............. A61J 1/2096 604/87 |
| 2011/0066107 A1* | 3/2011 | Stephens ............. A61M 5/3202 604/110 |
| 2011/0224616 A1* | 9/2011 | Slate ...................... A61M 5/20 604/154 |

OTHER PUBLICATIONS

Written Opinion for corresponding International Application No. PCT/US2013/035546, dated Jul. 26, 2013, 6 pages.

* cited by examiner

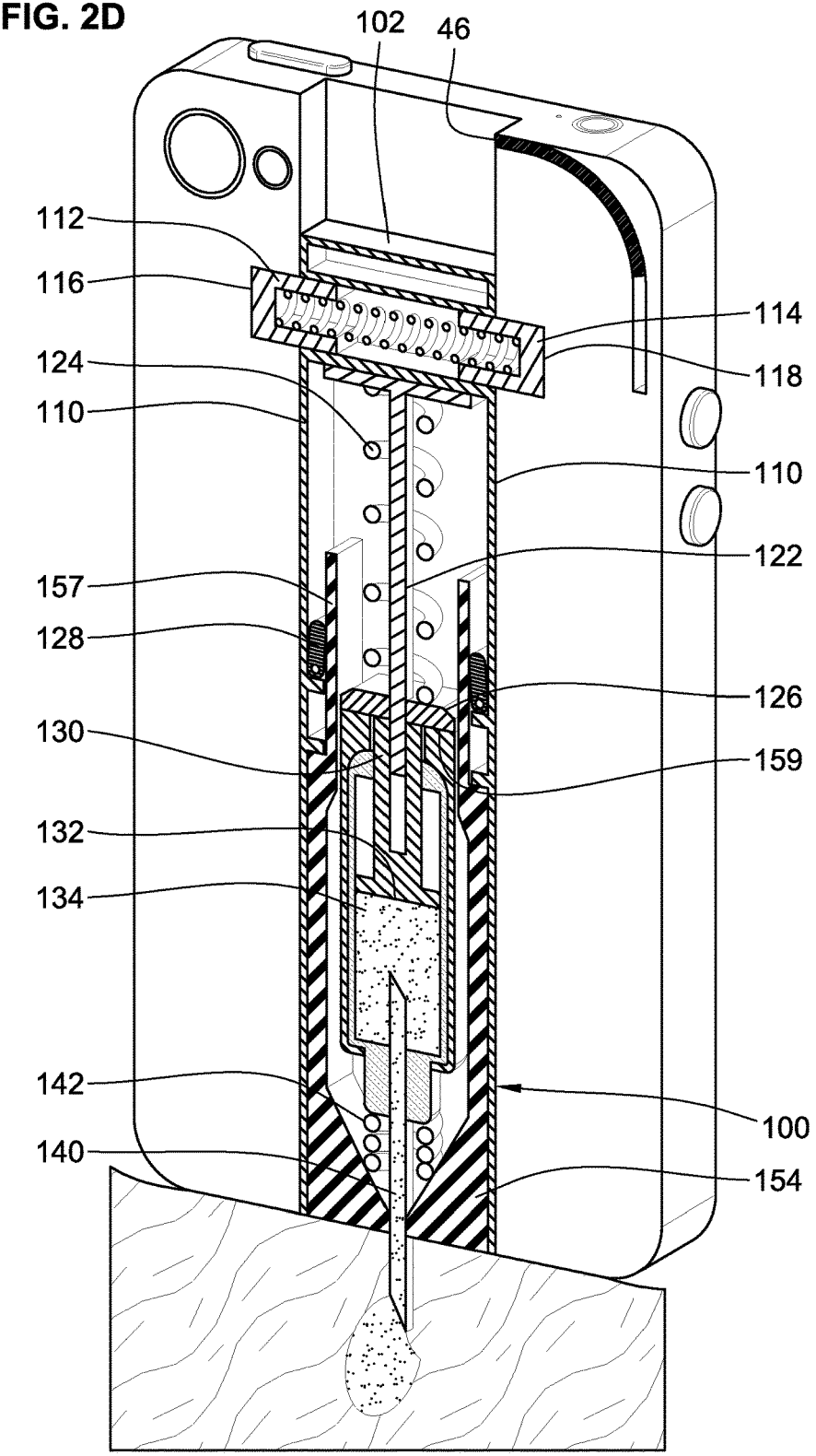

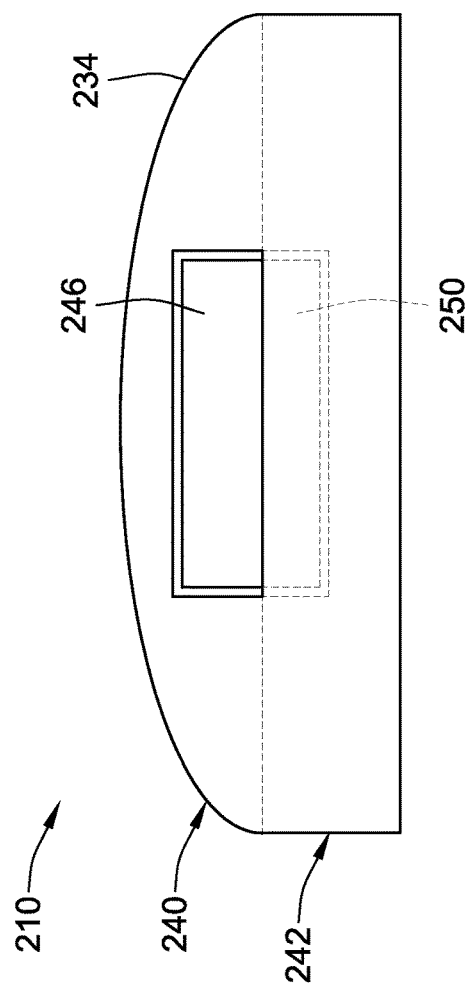
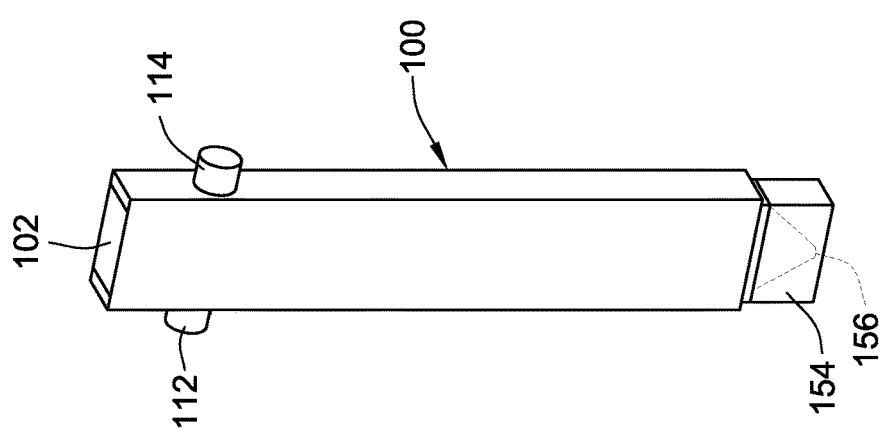

HYPODERMIC INJECTION DEVICE INCORPORATED IN A CASE FOR A PORTABLE ELECTRONIC DEVICE

CROSS REFERENCE TO RELATED APPLICATIONS

This application is the National Stage of International Application No. PCT/US2013/035546, filed Apr. 8, 2013, which claims the benefit under 35 U.S.C. § 119(e) of U.S. Provisional Application No. 61/622,681 filed Apr. 11, 2012, each of which is hereby incorporated by reference herein in its entirety.

FIELD OF THE INVENTION

The present invention generally relates to hypodermic auto-injection devices. More specifically, the present invention is directed to a hypodermic auto-injection device mounted within a case for a portable electronic device.

BACKGROUND

Auto-injection devices have been employed to inject epinephrine during emergency treatment of severe allergic reactions (anaphylaxis). Such devices are generally available by prescription to be carried by individuals having sufficiently severe allergic reactions. Available personal auto-injection devices are generally cylindrically-shaped devices that include an internally stored needle suitable for hypodermic injection. The needle is exposed during an injection sequence by penetrating a protective sheath. At the same time, a spring-loaded plunger is released to force an ampoule of epinephrine through the needle, thereby delivering a dose of epinephrine suitable to treat anaphylaxis. The amount of the dosage can be controlled by adjustable spacers or stops that control the depth of travel of the spring-loaded plunger.

While conventional auto-injectors are not in use, they are generally stored within protective cases. Such protective cases may have a hard outer shell and/or interior foam padding to protect the auto-injector from damage during falls and drops. Some cases are integrated into purses or handbags, while others are integrated into a leg strap or belt to allow the case to be carried by an individual. The cases may also include straps, handles, or clips to allow the individual to carry the auto-injector or to attach the auto-injector to other items they are carrying.

Personal electronic devices, such as cellular telephones, personal digital assistants, electronic readers, digital music players, etc., are typically stored in protective cases to prevent damage to the devices. In some instances, the cases are closely form-fitting and formed of a rigid material such as hard plastic. In other instances, cases for electronics can be formed of flexible cushioning foam or neoprene to protect the electronics against drops. Some cases for personal electronics include additional pouches, sleeves, etc., to hold items such as loose change, credit cards, make-up, etc. Other cases for personal electronics may include supplemental batteries for the device or circuitry to connect the device to a charging station while still connected to the case and via terminals integrated on the outside of the case.

SUMMARY

Aspects of the present disclosure provide a hypodermic injection device configured to be attached to a portable electronic device. The hypodermic injection device can be an auto-injector for delivering a dose of an injectable medicament. The injection device can include a durable barrier providing a sheath over an injectable cannula to maintain sterility of an injectable cannula that delivers the medicament. The injection device can also include tamper proof features such as by requiring that deployment of the device only be possible after completing two mechanical manipulations so as to prevent accidental discharge of the injection device. By incorporating the injection device within a case for a portable electronic device, the injection device is readily available to those that rely on auto-injectors to provide emergency therapeutic treatment, and is much less likely to be forgotten or left behind by a user than a typical auto-injector.

One of more aspects of the present disclosure provide a hypodermic injection device that includes an enclosure and a cartridge including a reservoir, a cannula, a spring-loaded plunger, a resilient sheath, and a release arm. The enclosure can have an internal cavity and can include a safety cover preventing access to a button while the safety cover is in a closed position. The cartridge can be situated within the cavity and configured to be slidably displaced within the cavity. The reservoir can house at least one dose of a fluid medicament. The cannula can have a first end configured for hypodermic injection, a second end opposite the first end, and an inner channel in fluid connection with the reservoir. The inner channel can terminate proximate the first end of the cannula. The spring-loaded plunger can be configured to urge the fluid medicament through the inner channel of the cannula responsive to release of a safety catch preventing actuation of the spring-loaded plunger. The resilient sheath can cover the first end of the cannula so as to maintain the cannula in a sterile condition. The release arm can be situated to release the safety catch responsive to the resilient sheath being urged toward the cannula. The cartridge can be configured to be urged from a first position, where the cannula is situated entirely within the internal cavity of the enclosure, to a second position, where the first end of the cannula extends from the internal cavity to an exterior of the enclosure. The cartridge can be urged to the second position in response to the depression of the button covered by the safety cover.

One or more aspects of the present disclosure provide a cartridge configured to be slidably mounted within a cavity of an enclosure configured to be securely attached to a portable electronic device. The cartridge includes a reservoir, a cannula, a spring-loaded plunger, a resilient sheath, and a release arm. The reservoir houses at least one dose of a fluid medicament. The cannula has a first end configured for hypodermic injection, a second end opposite the first end, and an inner channel in fluid connection with the reservoir. The inner channel terminates proximate the first end of the cannula. The spring-loaded plunger is configured to urge the fluid medicament through the inner channel of the cannula responsive to release of a safety catch preventing actuation of the spring-loaded plunger. The resilient sheath covers the first end of the cannula so as to maintain the cannula in a sterile condition. The release arm is situated to release the safety catch responsive to the resilient sheath being urged toward the cannula.

The injection devices described herein can be generally adapted for use with or without a ventilator. Additionally, the injection devices described herein can be adapted for use in any environment, including, but not limited to, at home, in clinics, in hospitals, or during transport from one place to another.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures:

FIG. 2D is a cross-sectional view of the portable electronics case shown in FIG. 2A with the spring-loaded plunger being deployed so as to inject a dose of the fluid medicament into the tissue.

FIG. 3 is a perspective view of the cartridge that is configured to be slidably mounted within a portable electronics case.

FIG. 4 is a bottom view of an alternative case with a cartridge including an injection device, where the case has a curved profile and a safety latch is moveable along a height dimension of the case, rather than along a width direction.

DETAILED DESCRIPTION

Figure 1A:
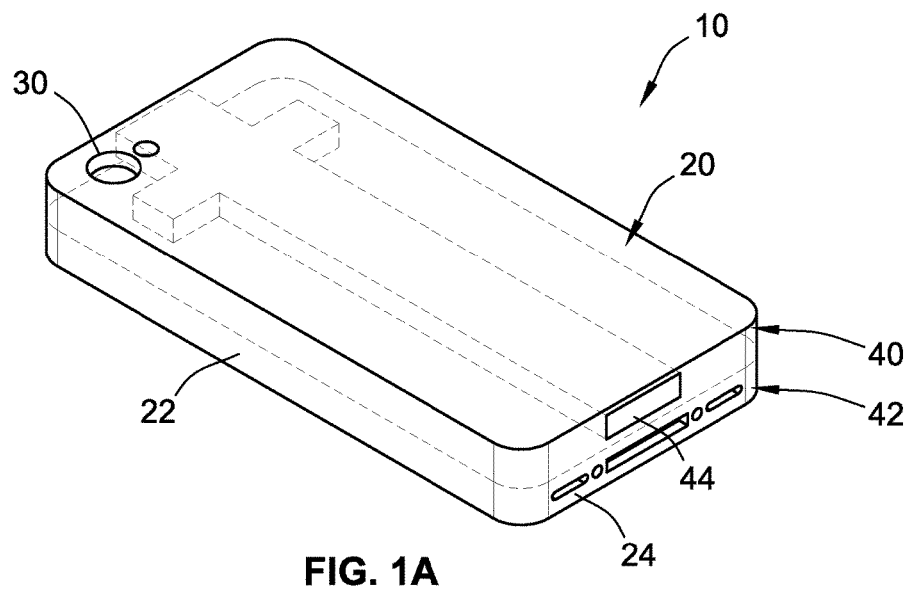
FIG. 1A is a perspective view of a portable electronics case with a cartridge including an injection device where a sheath covering the injection device is visible.
Figure 1B:
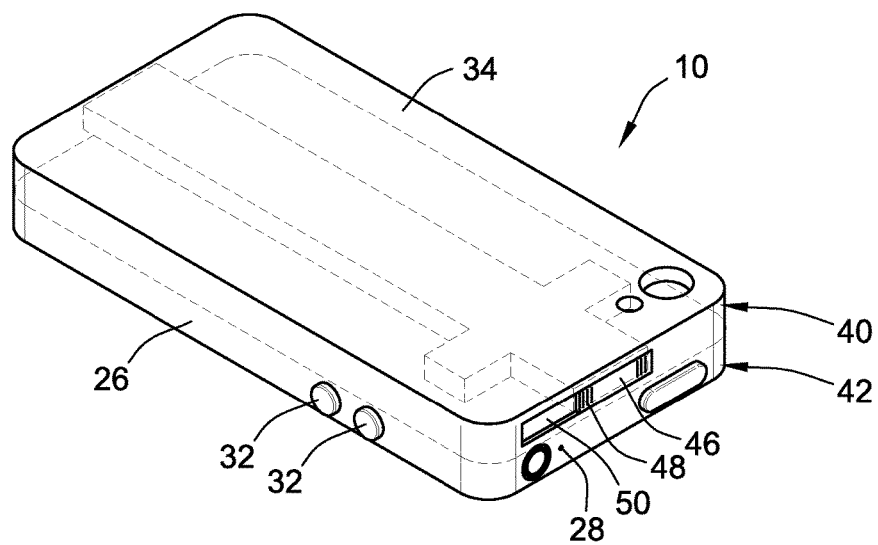
FIG. 1B is another perspective view of the portable electronics case shown in FIG. 1A where a safety cover preventing access to the injection device is visible.

FIG. 1A is a perspective view of a portable electronics case 10 with a cartridge including an injection device where a sheath 44 covering the injection device is visible. FIG. 1B is another perspective view of the portable electronics case 10 shown in FIG. 1A where a safety cover 46 preventing access to the injection device is visible. The case 10 shown in FIGS. 1A and 1B can be a case appropriate for securely containing a cellular telephone, personal digital assistant, digital music player, or similar device. For simplicity herein, the electronic device is described as a cell phone, it being understood that the present disclosure applies to cases attached to a range of personal electronic devices. The case 10 includes an exterior shell 20, which has an approximately rectangular back surface 34, and a first side 22 (visible in FIG. 1A), a second side 26 (visible in FIG. 1B), a bottom 24 (visible in FIG. 1A), and a top 28 (visible in FIG. 1B).

The case 10 has two portions, along a depth of the case 10 (a direction normal to the back surface 34): an injection portion 40, and a phone portion 42. A cell phone is mounted within the phone portion 42 of the case 10 by situating the cell phone within the phone portions while a display screen on the phone remains visible through an opening in the front side of the case 10 (not visible in FIGS. 1A and 1B, but generally opposite the back surface 34). Mounting the phone within the case 10 may be carried out by stretching, or otherwise manipulating, the sides 22, 26, top 28, and bottom 24 of the case 10 around the body of the cell phone so as to securely couple the case 10 to the cell phone. While mounted, a back side of the cell phone, opposite the side of the cell phone having the display screen, is situated adjacent to the injection portion 40. For example, the back side of the cell phone can be touching an internal wall of the case 10 that divides the phone portion 42 from the injection portion 40. Thus, in the views shown in FIGS. 1A and 1B, the phone portion 42 is faced downward, and the display of the cell phone mounted within the phone portion 42 is not visible.

However, various user-input and output ports and buttons on the phone are accessible through the case 10 on the sides 22, 26, top 28, and bottom 24. For example, two volume control buttons 32 are located on the second side 26. The buttons 32 may be integrated with the shell 20 and positioned so as to push against buttons on the phone located on corresponding positions of the side of the phone. Alternatively, the buttons 32 may be buttons on the phone that are accessible through apertures in the second side 26 of the shell 20. Similarly, the case can include one or more ports 30 to allow for operation of a camera and/or flash bulb included on the phone. Thus two ports 30 can be located on the back surface 34 of the shell 20 and positioned so as to align with a camera lens and a flash bulb located on the back side of the cell phone. The ports 30 thus pass through the entirety of the injection portion 40 and into the phone portion 42 of the case 10 such that a camera and/or flash bulb provided on the back side of the phone is operational while the phone is mounted within the case 10. Other buttons, apertures, ports, etc. may be included in the case 10 to allow features such as user-inputs, output jacks, microphones, speakers, audio jacks, power buttons, mute buttons, etc., of the phone to be accessible while the phone is mounted in the case 10. The location of the various ports (e.g., the ports 30), buttons (e.g., the buttons 32), etc., can be selected so as to align with input/output ports, etc., of particular cell phones or other personal electronic devices.

The case 10 also includes the injection portion 40. The injection portion 40 generally includes a hollow channel passing from the top 28 to the bottom 24 of the case 10, and an auto-injection cartridge (e.g., the cartridge 100 of FIG. 2A) mounted within the case. The internal structure and operation of the cartridge 100 will be described below in connection with FIGS. 2A through 2E. From the outside of the case 10, the cartridge is evidenced by a sliding safety latch 46, on the top 28, and a sheath surface 44, on the bottom 24. The sheath surface 44 covers the bottom side of the cartridge located within the hollow channel. The sheath surface 44 can be positioned to seal, at least temporarily, the bottom opening of the hollow cavity. In some instances, the sheath 44 includes a resilient barrier, such as a fluid-impermeable barrier to prevent contaminants from entering the cartridge and thereby maintain the cartridge in a sterile condition. The sheath surface 44 can be arranged generally co-planar with the bottom 24 of the shell 20. In some instances, the sheath 44 is color-coordinated with the shell 20 and/or formed of a material resembling the shell 20 such that the sheath surface 44 is not readily distinguishable from the surrounding regions of the bottom 24 of the shell 20.

The sliding safety latch 46 is located on the top 28 and is provided to prevent access to the cartridge located in the hollow cavity. When closed, the sliding safety latch 46 covers the top opening of the hollow cavity such that the cartridge located within the cavity cannot be accessed from outside the case 10. The latch 46 includes raised ridges 48 to provide a textured grip when sliding the latch 46 along the track 50 so as to move the latch 46 to an opened position. When opened, the latch 46 is moved to a position where the internal cavity is no longer covered, and the cartridge within the cavity can be accessed from outside the case 10. As shown in FIG. 1B, the track 50 is located along the top surface 28, however the track 50 can optionally be at least partially internal to the case 10, as shown in FIGS. 2A through 2E so long as the latch 46 is able to be displaced from a closed position, where the cartridge is covered, to an opened position, where the cartridge is uncovered.

Figure 2A:
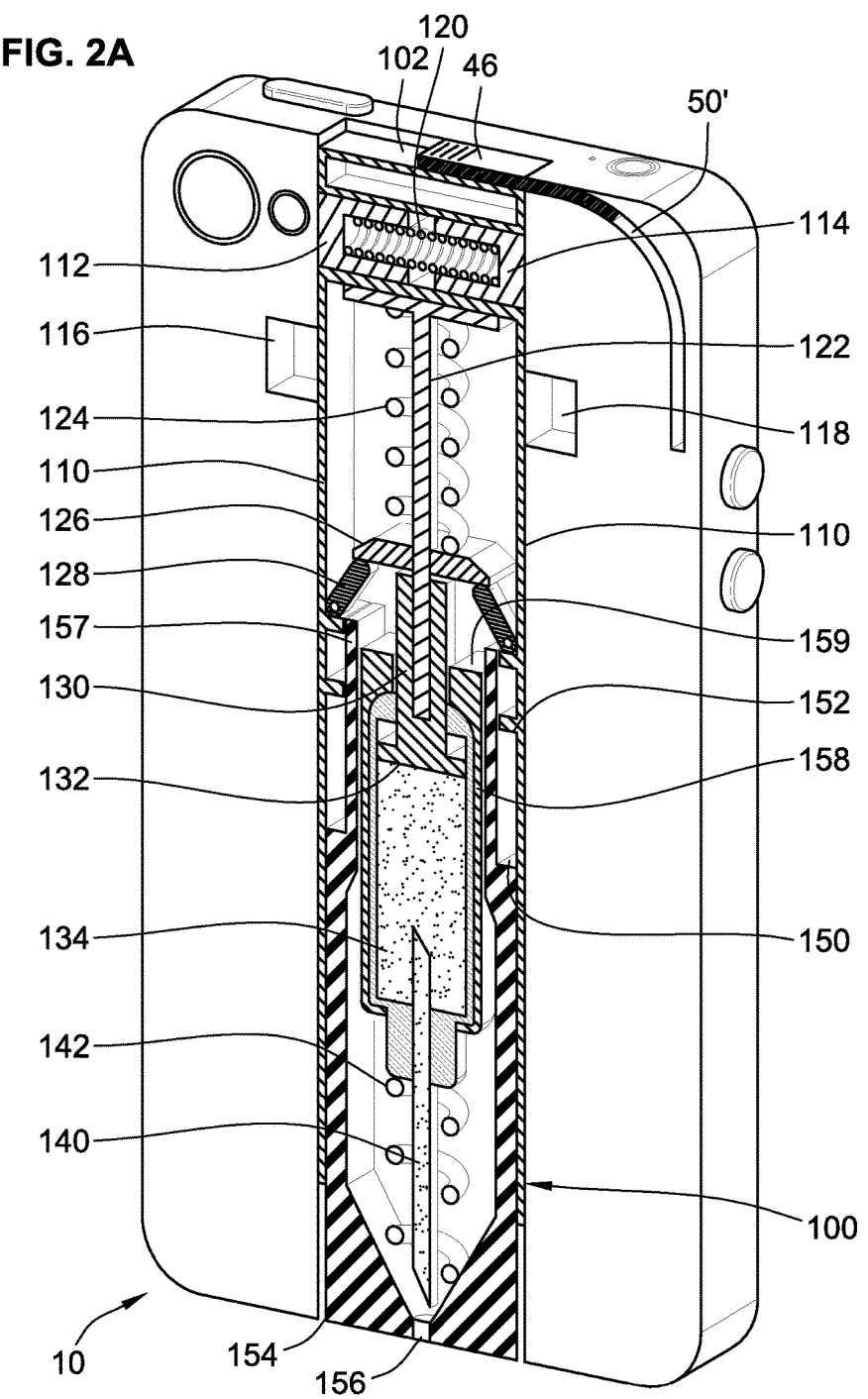
FIG. 2A is a cross-sectional view of the portable electronics case shown in FIG. 1A where the auto-injector cartridge is not deployed and the safety cover partially covers the cartridge.
Figure 2A:

FIG. 2A is a cross-sectional view of the portable electronics case shown in FIG. 1A where the auto-injector cartridge 100 is not deployed. The cartridge 100 is mounted within the hollow cavity of the phone portion 40 of the case 10. Within the cartridge 100, a reservoir 134 is loaded with at least one dose of a fluid medicament. A cannula 140 has an interior channel in fluid connection with the reservoir 134 and includes an end configured for hypodermic injection. In some instances, the cannula 140 is rigidly connected to the reservoir 134. A plunger 132 seals one end of the reservoir 134 such that forcing the plunger 132 into the reservoir 134 pushes the fluid medicament through the cannula 140. The operation of the auto-injector cartridge 100 to provide a dose of fluid medicament will be described in connection with FIGS. 2B through 2E, which illustrate the cartridge 100 in various states during an injection operation.

Figure 2B:
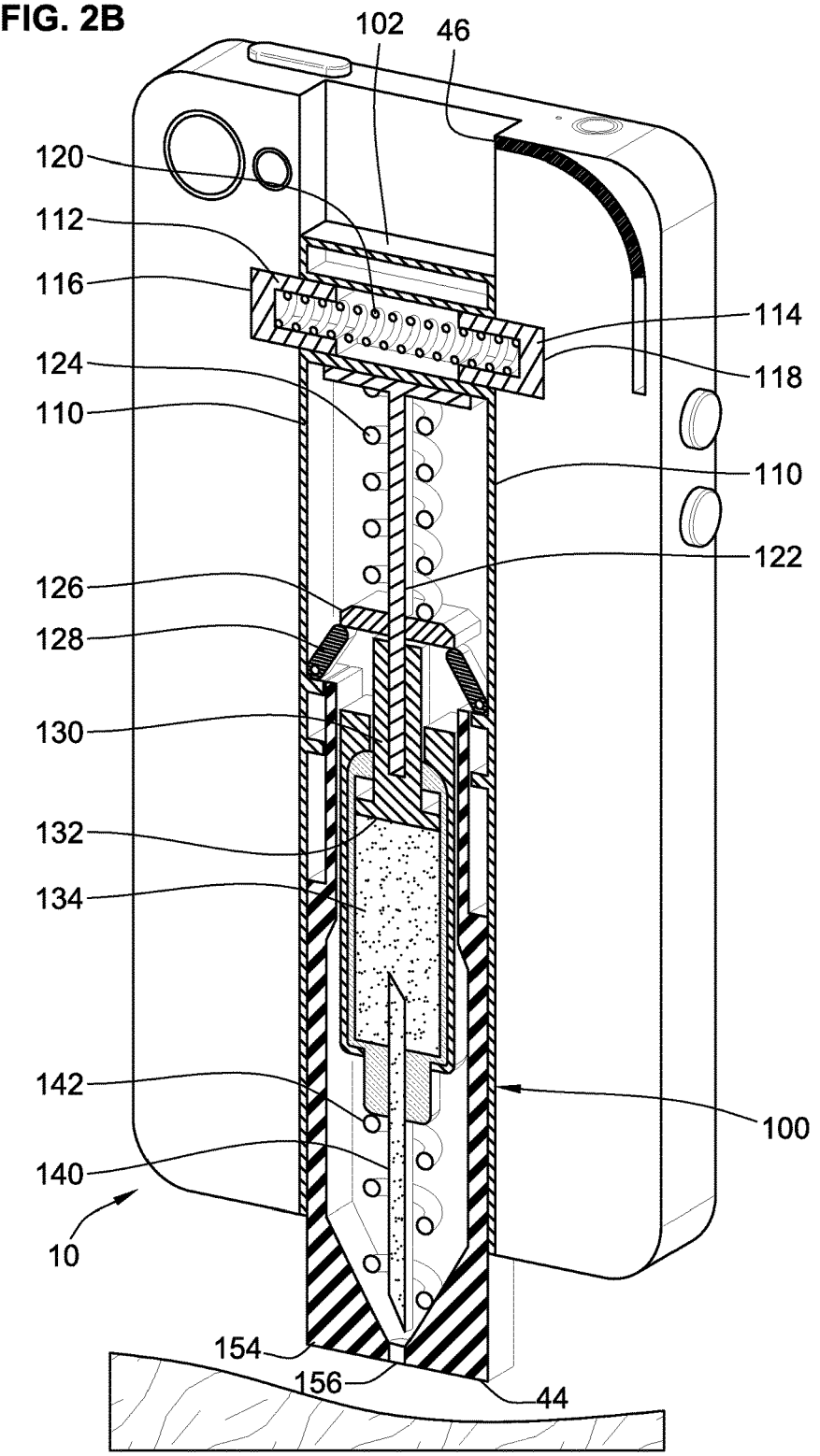
FIG. 2B is a cross-sectional view of the portable electronics case shown in FIG. 2A with the cartridge is engaged in a deployed position by actuation of the locking pins with ports within the case.

Referring to FIG. 2A, the cartridge 100 includes a housing 110 having side walls that enclose the cartridge 100 and provide structural support for the various components mounted within the cartridge 100. The side walls of the housing 110 extend along the length of the cartridge 100. However, the side walls of the housing 110 may not extend the entire length of the cartridge 100, and may be shorter than the cartridge by an amount determined by the displacement of the cartridge when it is slidably moved to the deployed position (as shown in FIG. 2B). Such a configuration allows the cartridge 100 to be engaged in the deployed position while the housing 110 remains generally within the case 10. As will be explained in connection with FIG. 2D, keeping the housing 110 substantially within the case 10 avoids undesirable interference with the operation of the injection device. Thus, the bottom portion of the housing 110 is open, such that components within the cartridge 100 including the cannula 140 can slide in and out of the open bottom end of the housing 110. The external bottom end of the cartridge 100 is therefore formed by the sheath 154, which extends from the bottom of the housing 110 by an amount given by the displacement of the cartridge 100 when it is slidably moved to the deployed position.

The side walls of the housing 110 can optionally have outward-facing ridges along the length of the cartridge 100 configured to engage matching channels within the hollow cavity of the case 10 so as to provide a track along which the cartridge 100 is slidably moved within the case 10. Additionally or alternatively, the outward-facing sides of the housing 110 (i.e., the side of the housing 110 situated against the internal walls of the hollow cavity within the case 10) can include wheels or smooth gliding pads arranged to ride on rails or tracks defined in the hollow cavity.

Referring again to FIG. 2A, the top-most portion of the housing 110 defines a depressible button 102. The safety cover 46 is shown being moved between its closed position, where it completely covers the button 102, and its opened position, where the button 102 is accessible from the exterior of the case 10. The safety cover 46 is partially recessed within the recessed channel 50'. The portion of the housing 110 defining the button 102 covers a hollow region in the housing containing two locking pins 112, 114. The locking pins 112, 114 are outwardly-biased, with respect to the housing 110, by a spring 120 that urges both pins 112, 114 away from one another. Of course, in an alternative configuration, the housing 110 can include a center wall bisecting the hollow region and separate springs can be mounted on opposing sides of the center wall to provide an outward bias to the first locking pin 112 and the second locking 114, respectively. The outward bias is provided by compressing the spring 120 beyond its natural compression such that the pins 112, 114 are urged outwardly away from the housing and against the inner walls of the hollow cavity in the case 10. Of course, alternatively elastic elements can be substituted for the spring 120 to provide the outward biasing of the pins 112, 114.

Two ports 116, 118 are defined within the hollow cavity in the case 10. The ports 116, 118 are dimensioned to receive the locking pins 112, 114 and are positioned such that urging the cartridge 100 downward, by pushing the button 102 in to the case 100, moves the pins 112, 114 to align with the ports 116, 118. For example, the ports can be located further, along the length of the hollow cavity, from the top side 28 of the case 10 (and the button 102) than the locking pins 112, 114, such that the locking pins 112, 114 are not aligned with the ports 116, 118 while the cartridge remains in the not deployed position shown in FIG. 1A.

On the other side of the hollow region housing the pins 112, 114, the cartridge 100 includes an injection spring 124 coiled around a guide rod 122. The guide rod 122 is internally mounted within the housing to be generally central and oriented along the length of the cartridge. The guide rod 122 both retains the injection spring 124 and directs a travel path for the plunger 132 within the reservoir 134, as will be discussed in connection with FIG. 2D. The injection spring 124 pushes against a stop plate 126 that is biased downwardly, i.e., away from the button 102 on the top side of the cartridge 100, by the injection spring 124. The injection spring 124 can be compressed to smaller than its unbiased ("resting") compression length to allow the stop plate 126 to be downwardly biased. The guide rod 122 extends through the stop plate 126 and is telescopically received by a plunger rod 130 on the other side of the stop plate 126.

Figure 2C:
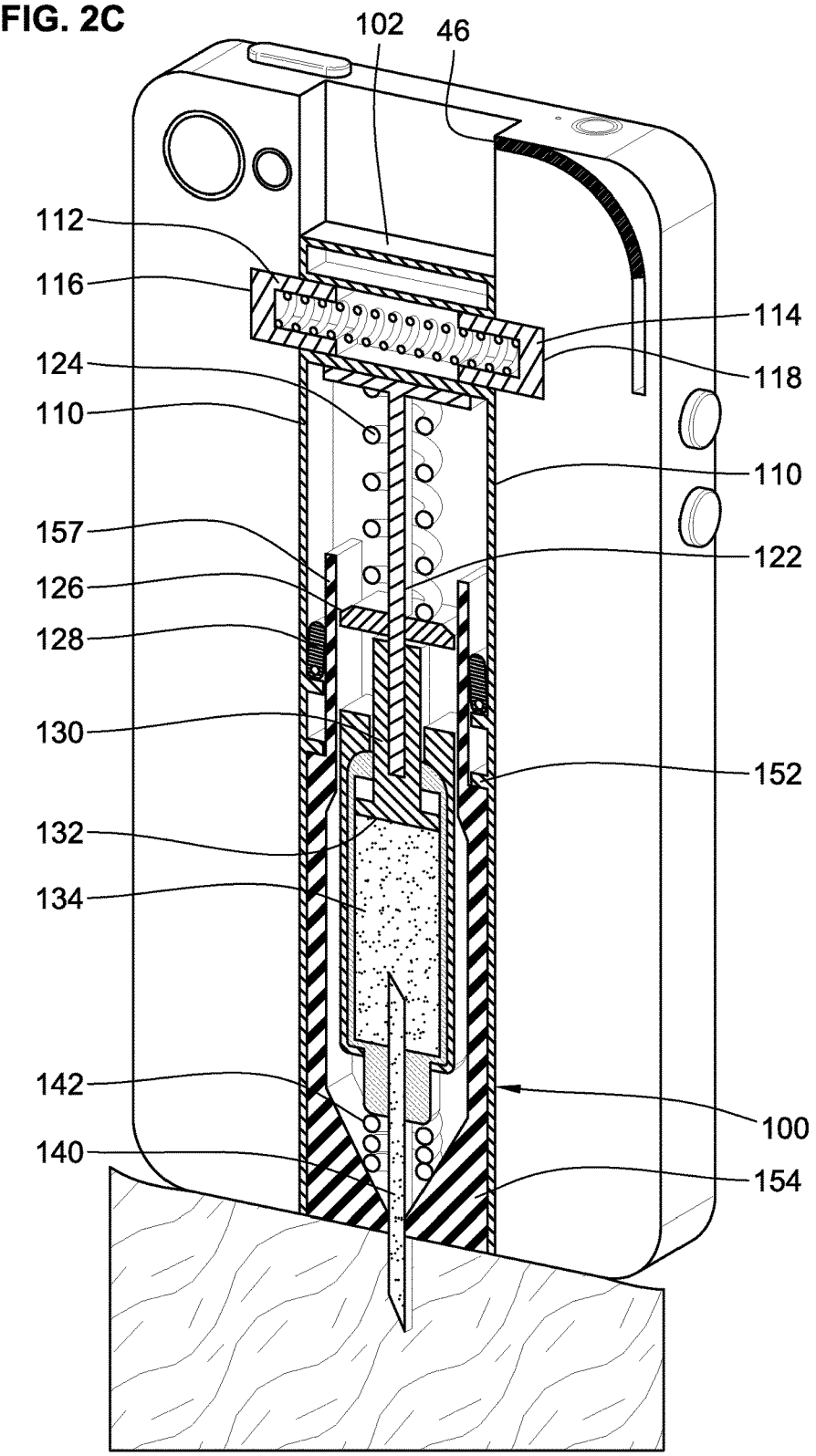
FIG. 2C is a is a cross-sectional view of the portable electronics case shown in FIG. 2A with the sheath pushed into the cavity by contact with tissue such that the cannula extends past the sheath and into the tissue.

The side of the stop plate opposite 126 the injection spring 124 rests against pivoting safety catches 128. The safety catches 128 keep the stop plate 126 in place against the biasing force from the injection spring 124, which is applied to the opposite side of the stop plate 126. The pivoting safety catches 128 are mounted to the internal side walls of the housing 110 on pivots that allow the safety catches 128 to pivot outwardly from the walls of the housing 110 to an extended position, where the catches engage the stop plate 126, as shown in FIG. 2A. The catches 128 can also pivot to a release position as to be nearly flush against the internal walls of the housing 110, where the stop plate 126 is not engaged by the catches 12, as shown in FIG. 2C.

The plunger rod 130 that telescopically engages the guide rod 122 is rigidly connected to the plunger 132 such that urging the plunger rod 130 downward (away from the button 102 on the top of the cartridge 100) depresses a plunger 132 within the reservoir 134. The reservoir 134 is mounted within the cartridge 100 by a mounting 158 that is securely connected to the housing 110. The mounting 158 is securely attached to the reservoir 134 so as to securely couple the reservoir 134 to the housing 110. The mounting 158 can be arranged to substantially surround the sides and upper and lower indented lips of the reservoir 134 as shown in FIGS. 2A through 2E, or can be disposed to surround only such portions of the reservoir 134 as are necessary to securely connect (e.g., rigidly connect) the reservoir 134 to the housing 110. While shown in cross-section, the mounting 158 can be connected to internal walls of the housing 110 which are not visible due to the cross-section view. Due to the mounting 158, the reservoir 134 is arranged to be co-moving with the housing 110.

The cannula 140 is rigidly connected to the reservoir 134 and arranged to extend from the reservoir 134 opposite the plunger 132. The cannula 140 is an injection needle, such as a commonly utilized medical needle for injections of fluid medicaments under the skin. The end of the cannula 140 extending from the reservoir 134 is an injection end suitable for hypodermic injection. The end of the cannula 140 opposite the injection end is rigidly connected to the reservoir 134. An internal channel within the cannula 140 is in fluid connection with the reservoir 134 and terminates near the injection end of the cannula such that the cannula can be employed to hypodermically inject fluid medicaments from the reservoir 134, through the internal channel in the cannula. A rebounding spring 142 surrounds the cannula 140 extending from the reservoir 134 to bias the cannula 140 within the sheath 154. The rebounding spring 142 can be arranged to be slightly compressed, relative to its resting length, while the cannula 140 is situated entirely within the sheath 154 (i.e., not protruding from the exit point 156 in the sheath 154), as shown in FIG. 2A. The compression of the rebounding spring 142 provides a bias between the reservoir 134 and the sheath 154 to maintain the cannula 140 within the sheath 154.

The sheath 154 protrudes from the open bottom end of the housing 110 to form the bottom end of the cartridge 100. On the exterior of the case 10, the sheath 154 forms the sheath surface 44 discussed in connection with FIG. 1A. The sheath 154 extends into the cartridge 100, along the side walls of the housing 110, on either side of the mounting 158 surrounding the reservoir 134. The sheath 154 is configured to slide into the cartridge 100, through the opening in the bottom of the housing 110, as will be described in connection with FIG. 2C. The sheath 154 includes release arms 157 aligned to engage the pivoting safety catches 128 when the sheath 154 is urged upward into the cartridge 100 (toward the button 102).

FIG. 2B is a cross-sectional view of the portable electronics case 10 shown in FIG. 2A with the cartridge 100 engaged in the deployed position by actuation of the locking pins 112, 114 with the ports 116, 118 within the case. The latch 46 is moved entirely within the recessed channel 50' such that the button 102 is exposed from the outside of the case 10. The button 102 is pressed downward into the case 10 to move the cartridge through the hollow cavity in the case 10 far enough that the locking pins 112, 114 are aligned with ports 116, 118. The locking pins 112, 114 expand from the hollow region, under force of the spring 120, to engage the ports 116, 118, and thereby securely couple the cartridge 100 to the case 10 in the deployed position.

The dimensions of the locking pins 112, 114, and the ports 116, 118, are selected such that a portion of the pins 112, 114 remain within the hollow region of the cartridge 100 while the pins 112, 114 are fully seated in the ports 116, 118. For example, the pins 112, 114 can have a length exceeding the depth of the ports 116, 118, such that the pins 112, 114 can be fully seated within the ports 116, 118 while a portion of the pins 112, 114 remains within the hollow region of the cartridge 100. By allowing for the pins 112, 114 to simultaneously engage the ports 116, 118, and the hollow region in the housing 110, the housing 110 is securely coupled to the case 10. Once engaged, the locking pins 112, 114 prevent the cartridge 100 from moving within the hollow cavity of the case 10 by securely coupling the housing 110 to the internal walls of the hollow cavity in the case 10. In particular, in the deployed position shown in FIG. 2B, the cartridge 100 does not continue to travel downward through the case 10 even if urged downward by a force on the button 102.

In the deployed position, the side walls of the housing 110 terminate near the bottom 24 of the case 10, without protruding from the case 10. At the same time, the lowest portion of the cartridge 100, formed by the sheath 154, protrudes from the bottom 24 of the case 10. Moving the housing 110 to the deployed position also moves the reservoir 134 by the same amount as the button 102 due to the connection between the reservoir 134 and the mounting 158. The cannula 140 is rigidly connected to the reservoir 134 and is also displaced by the depression of the button 102. In the deployed position, the injection end of the cannula 140, protrudes from the case 10 such that the cannula 140 breaks an imaginary plane defined by the bottom 24 of the case 10. The cannula 140 remains entirely within the sheath 154 by action of the rebound spring 142, which maintains the separation between the reservoir 134 and the internal edge of the sheath 154 at substantially the same distance as in the non-deployed position shown in FIG. 2A, so long as no external forces act on the sheath 154 to compress the rebound spring 142.

While in the deployed position, the sheath 154 maintains the sterility of the inner portion of the cartridge 100, and particularly the cannula 140 and the reservoir 134. The sheath 154 can include an integrated resilient barrier, such as a fluid-impermeable barrier, to provide a sterile covering over the bottom of the cartridge 100 and thereby prevent contamination of the cannula 140 or the fluid medicaments within the reservoir 134. In some embodiments, the cartridge 100 can include a sterility indicator visible through a window through the sheath surface 44 forming the bottom of the sheath 154. The sterility indicator can be a color-changing element that reacts by changing color in response to indicators of sterility being compromised within the cartridge 100, such as indicators based on chemical signatures, optical signatures, temperature, etc. Situating a sterility indicator visible from the exterior of the case 10 allows a user to determine whether the contents of the cartridge 100 remain sterile and suitable for use as a hypodermic injection device, and thereby determine whether the cartridge 100 and/or case should be replaced.

FIG. 2C is a is a cross-sectional view of the portable electronics case 10 shown in FIG. 2A with the sheath 154 pushed into the cavity by contact with tissue such that the cannula 140 extends past the sheath and into the tissue. The cannula 140 exits the sheath 154 at the exit point 156. In examples where the sheath 154 includes an integrated resilient barrier configured to maintain the sterility of the cannula 140, the resilient barrier can cover the exit point 156 and the exit of the cannula 140 through the exit point 156 can be achieved by the cannula 140 piercing the resilient barrier.

The sheath 154 extends into the cartridge 100, along the internal side walls of the housing 110. The extended portions of the sheath 154 advantageously is configured to slide along the internal side walls of the housing 110. The extended portions of the sheath 154 include a shoulder 150 where the sheath narrows to form the release arms 157. At the shoulder 150, the sheath 154 extends away from the side walls of the housing 110 by a distance corresponding to the ledge 152, which protrudes from the side wall 110 at a location upward from the shoulder 150, i.e., closer to the button 102 forming the top of the cartridge 100. The ledge 152 is securely coupled to the side wall of the housing 110.

The ledge 152 and the shoulder 150 combine to define an inward limit to the travel path of the sheath 154 into the housing 110. The release arms 157 are located interior to the ledge 152 (i.e., closer to the guide rod 122 in the center of the cartridge 100), such that the release arms 157 travel inward without interfering with the ledge 152. The length of the release arms 157 and the locations of the shoulder 150 and ledge 152 are selected such that during the inward travel of the sheath 154, the release arms 157 engage the pivoting catches 128 prior to the shoulder 150 stopping against the ledge 152. The location of the ledge 152 can also be selected to allow the sheath 154 to be nearly entirely within the case 10 when the shoulder 150 engages the ledge 152. For example, the sheath surface 44 forming the bottom surface of the sheath 154 can be approximately co-planar with the bottom 28 of the case 10 when the shoulder 150 engages the ledge 152.

The release arms 157 are securely connected to the sheath 154 such that moving the sheath 154 upward with respect to the housing 110 such that the sheath 154 is urged into the open bottom of the housing 110 in the cartridge 100, causes the release arms 157 to push the safety catches 128 to pivot about their respective axes away from the stop plate 126 and toward the internal walls of the housing 110.

The lowest portions of the sheath 154 (including the sheath surface 44), the release arms 157, and the extended portions of the sheath 154 (including the shoulder 150 and the release arms 157) can either be distinct components securely connected to one another, can be integrally formed with one another, or some combination thereof.

FIG. 2D is a cross-sectional view of the portable electronics case shown in FIG. 2A with the spring-loaded plunger 132 being deployed so as to inject a dose of the fluid medicament into the tissue. Once the safety catches 128 are pivoted to be flush against the internal walls of the housing 110, as shown in FIG. 2C, the stop plate 126 is no longer held in place between the safety catches 128 and the injection spring 124. Once released the stop plate 126 slides past the guide rod 122 to move downwardly, with respect to the housing 110, under the force of the injection spring 124. The stop plate 126 engages the plunger rod 130 and urges the plunger rod 130 downwardly (away from the button 102 at the top of the cartridge 110), which causes the plunger 132 to be depressed in the reservoir 134. The plunger rod 130 travels downward along the path defined by the guide rod 122, which is telescopically engaged in the plunger rod 130 to allow the plunger rod 130 to move up and down along the length of the guide rod 122. The downward movement of the plunger 132 exerts a hydraulic pressure on the fluid medicament stored in the reservoir 134, which is urged through the cannula 140 and into the tissue, as shown in FIG. 2D. The injection of a dose of the fluid medicament into the tissue can require that the case be left in place against the tissue for a brief period, which will generally depend on the gauge of the cannula 140, the strength of the injection spring 124, and the viscosity of the fluid medicament in the reservoir 134. The injection spring 124 is generally stronger than the rebound spring 142 to prevent the force from the rebound spring 142 from interfering with the injection sequence.

The dose of the delivered fluid medicament is thus determined at least in part according to an initial separation, before injection, between the stop plate 126 and the stop surface 159. The separation between the stop plate 126 and stop surface 159 controls the vertical travel distance of the plunger 132 within the reservoir 134. By selecting the vertical travel distance of the plunger 132 in the reservoir 134, the volume of fluid displaced by the plunger 132 can be selected to correspond to a single dose of the fluid medicament. Thus, in examples where the cartridge is a hypodermic auto-injector for epinephrine, different initial locations for the stop plate 126 are suitable for adult users and child users, for example.

Figure 2E:
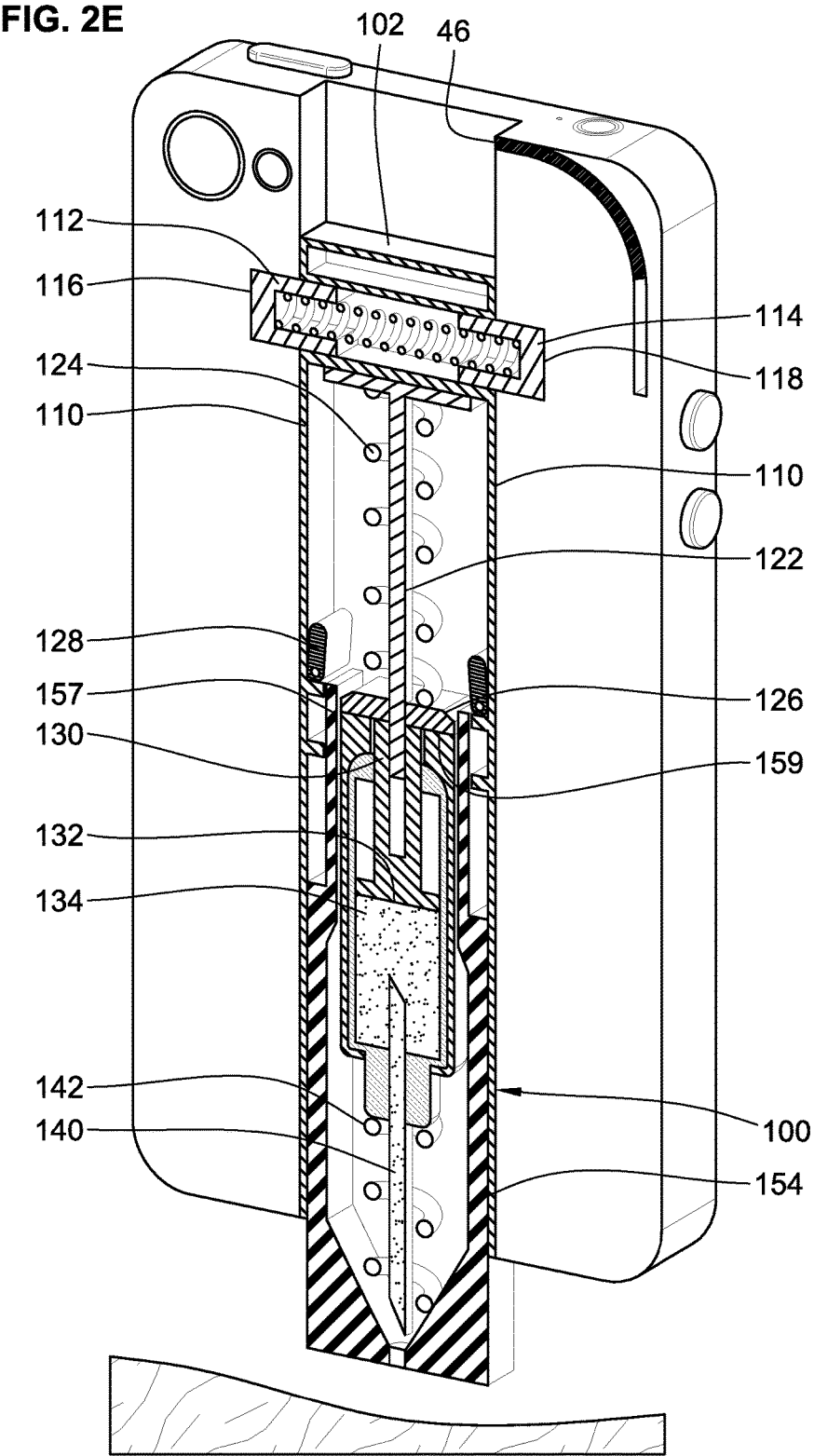
FIG. 2E is a cross-sectional view of the portable electronics case shown in FIG. 2A with the cannula retracted from the tissue and enclosed within the sheath.

FIG. 2E is a cross-sectional view of the portable electronics case shown in FIG. 2A with the cannula 140 refracted from the tissue and enclosed within the sheath 154. Following injection, the case 10 is urged away from the tissue, which withdraws the cannula 140 from the tissue due to the secure coupling between the cannula 140 and the case 10 via the mounting 158. As the cannula 140 is withdrawn from the tissue, the sheath 154 extends to cover the cannula 140 again, under force of the rebound spring 142. Once the cannula 140 is fully withdrawn from the tissue, the sheath 154 moves to the protruding position to enclose the cannula 140 again, which concludes the injection sequence. Enclosing the cannula 140 following the injection prevents the cannula 140 from being inadvertently exposed to another person, which increases safety of those handling the cartridge 100 following the injection sequence. However, the cartridge 100 is not entirely reset to its initial position following the injection sequence. As shown in FIG. 2E, the cartridge 100 remains in the deployed position via the pins 112, 114 and the plunger 132 remains at the position in the reservoir 134 defined by the stop surface 159.

In operation, the case 10 can be used to provide an emergency injection of the fluid medicament stored in the reservoir 134. An individual carrying the case 10 first manipulates the cartridge 100 to the deployed position by sliding the safety latch 46 into the recessed channel 50' to uncover the button 102, as in FIG. 2A. Once uncovered, the individual can press the button 102 downward, into the hollow cavity of the case 10 such that the sheath 154 (and the cannula 140 within the sheath 154) protrudes from the opposite side of the case 10, as in FIG. 2B. The button 102 is pushed downward until the locking pins 112, 114 engage the ports 116, 118 to hold the cartridge 100 in the deployed position. The bottom 28 of the case 10 with the protruding sheath 154 is then firmly pressed against tissue, such as a thigh, and the sheath 154 is urged in to the case 10 while the cannula 140 is held in position by its secure connection with the housing 110 (via the mounting 158 securing the reservoir 134), as in FIG. 2C. The cannula 140 exits the sheath 154 at the exit point 156 and the injection end of the cannula 140 enters the tissue. As the sheath 154 continues to travel upward into the cartridge 100, release arms 157 connected to the sheath 154 release pivoting safety catches 128, which is shown in FIG. 2C. The safety catches 128 release an injection spring 124 to push against a plunger 132 (via the plunger rod 130), as shown in FIG. 2D. The pressure on the plunger 132 hydraulically forces fluid medicament in the reservoir 134 through the cannula 140 and into the tissue, shown in FIG. 2D. The case 10 is held firmly against the thigh while the fluid medicament is injected under force of the injection spring 124. The injection of the fluid medicament continues until the stop plate 126 strikes the stop surface 159 connected to the housing 110. Upon pulling the case 10 away from the tissue, the sheath 154 initially maintains contact with the thigh under force of the rebound spring 142, such that the cannula 140 is shielded by the sheath 154 as it is withdrawn. The cannula 140 is removed from the tissue and surrounded again by the sheath 154, which returns the sheath to the protruding position shown in FIG. 2E.

Various features and components of the cartridge 100 described in connection with FIGS. 2A through 2E are described for convenience with respect to "top," "bottom," "left," "right," "downward," "upward," and similar terms of orientation for clarity in referring to the drawings. However, it is noted that the orientation of the features of the cartridge 100 will be dependent on the orientation of the cartridge and may be rotated depending on the orientation of the cartridge 100, and that references to a top side, or a bottom side, for example, may also refer to a first side, and a second side, respectively.

FIG. 3 is a perspective view of the cartridge 100 that is configured to be slidably mounted within a portable electronics case 10. The cartridge 100 can be a generally rectangular three-dimension object with a height, a width, and a depth. The height can be greater than the width, and the width can be greater than the depth, and the features within the cartridge 100 can be arranged to spread along the width direction of the cartridge, rather than along the depth direction, to provide a slim profile for the cartridge 100 within the case 10. The height of the cartridge 100 can be determined based on the size of the case 10, which can be determined according to the dimensions of the phone held within the case 10. The depth of the cartridge 100 generally corresponds to the amount of thickness the case 10 adds to the profile of the phone, i.e., the thickness of the injection portion 40. The width of the cartridge 100 is determined according to the requirements to fit the various components within the case, given the restrictions on depth. For example, the reservoir 134 can be wider, along the width direction, than along the depth direction, to allow the cartridge 100 to have a slimmer profile and thereby decrease the total thickness of the case 10.

In some instances, features such as the reservoir 134, the stop plate 126, etc., are not cylindrically symmetrical about the central axis through the cartridge 100 defined by the guide rod 122 and the cannula 140, and instead are arranged to extend in an elliptical or rectangular arrangement, elongated along the width direction. In some examples, cartridge 100 is configured to be sufficiently slim that the total thickness of the injection portion 40 is less than ⅜ of an inch.

FIG. 4 is a bottom view of an alternative case 210 with a cartridge including an injection device, where the case has a curved back surface 234 and a safety latch 246 is moveable along a height dimension of the case, rather than along a width direction. The alternative case 210 includes a phone portion 242, which can be similar to the phone portion 42 of the case 10, and an injection portion 240. The injection portion 240 includes a hollow cavity suitable for being loaded with the cartridge 100, similar to the hollow cavity in the case 10. The safety latch 246 is situated to cover the hollow cavity, when in a closed position to prevent access to the cartridge in the cavity. Similar to the safety latch 46 in the case 10, the safety latch 246 is configured to slide to an open position where the cartridge can be accessed. The safety latch 246 slides along a channel 250 defined in the case 210.

The channel 250 extends toward the phone portion 242 of the case 210, from the injection portion 240, along the height of the case 210. Similar to the movement of the safety latch 46 in the case 10, the safety latch 246 is moved in a direction perpendicular to the direction of the depression of the button such that deployment of the cartridge requires a two-step operation with manipulations in two distinct directions. Providing a two-step procedure to deploy the cartridge reduces incidences of accidental deployment.

The curved back surface 234 gives the alternative case 210 a reduced profile, in comparison to the case 10. However, the alternative case 210 can have a hollow cavity for housing the cartridge that is equivalent in dimensions to the hollow cavity in the case 10 described above in connection with FIGS. 1-2.

In at least some examples, the function of the auto-injection cartridge 100 to hypodermically deliver fluid medicaments is performed entirely without reliance on electrical power. In some examples, the auto-injection cartridge 100 is operated via mechanical elements only, such as the operation of the button 102 and locking pins 112, 114, the forces from the springs 120, 124, 142, and the movement of the pivoting catches 128 via the release arms 157. By configuring the cartridge 100 to provide hypodermic delivery of fluid medicaments via mechanical elements only, the cartridge 100 operates in the absence of any electrical power source, which allows the cartridge 100 to be operated in an emergency without reliance on electrical power.

Generally, the cartridge 100 is a one-time use auto-injector device. Thus, after a single use, the cartridge 100 and/or case 10 can be replaced. Replacing the cartridge 100 and/or case 10 after a single use circumvents problems with refilling the reservoir 134 with an appropriate dose of fluid medicaments, un-seating the locking pins 112, 114 from the ports 116, 118, and re-sterilizing the cannula 140 and the contents of the reservoir 134 to be suitable for hypodermic injection. In some instances, the case 10 can be marketed with a shelf life comparable to available auto-injector devices containing single doses of fluid medicaments, such as auto-injector devices for epinephrine, insulin, etc. In other instances, the cartridge 100 can be a refillable cartridge that is removable from the case 10 after a single use and re-sterilized before inserted again.

In an emergency, an individual in need of hypodermically injected fluid medicaments carrying a cellular phone in the case 10 can rapidly transform the case to a hypodermic auto-injector by moving the cartridge 100 to the deployed position. Once in the deployed position, the protruding sheath 154 containing the cannula 150 and firmly pressing the protruding cannula 140 (situated within the protruding sheath 154) case against tissue to be injected. By situating the hypodermic injection cartridge 100 within a case for a personal electronic device, such as a cellular phone, an individual in need of emergency delivery of hypodermically injected fluids is no longer required to travel with a separate auto-injection device. Individuals with severe allergic reaction that have previously carried separate auto-injection devices are now less likely to inadvertently leave behind their auto-injection device, because it is integrated within the case for the cellular phone (or other personal electronic device).

In still further examples, the cartridge 100 can be configured to alert emergency personnel upon deployment of the device. In cooperation with the phone (or other communicative personal electronic device housed in the case 10), emergency notification signals can be sent to emergency personnel and/or designated emergency contacts to indicate that the auto-injection device has been deployed. The emergency notification signals can be generated according to a processor executing instructions stored in a memory of the phone and can include indicators of the location of the phone based on GPS signals or other coordinate indicators, such as locations derived from cell phone tower strengths and/or detected Wi-Fi connections, etc. The emergency notification signals can also include information indicative of known allergens, diabetic conditions, and/or other pertinent medical information of the carrier of the case to be used by emergency response personnel. Automatically generating emergency notification signals as described herein desirably enhances emergency response times for individuals suffering from anaphylaxis.

The generation of the emergency notification signals can be carried out in response to signals from a sensor located in the cartridge that is arranged to detect the movement of the cartridge 100 to the deployed position. In some instances, a pressure sensitive sensor, such as button, can be situated at the internal wall of one or both of the ports 116, 118 such that the sensor is pressed when the pins 112, 114 are locked in place in the ports 116, 118. Providing signals to the phone can be accomplished by a wireless connection, such as a Wi-Fi connection, a Bluetooth® connection, etc. Some examples that notify the phone via wireless signals can be carried out by a wireless signal generator within the injection portion of the case powered by a power source, such as a battery, with a stable operating life comparable to the expiration term of the fluid medicaments in the cartridge.

In other examples, the deployment of the cartridge 100 can be detected entirely by the phone, without receiving a separate signal from the case 10. For example, the phone can operate software configured to detect characteristic sounds and/or vibrational feedback associated with the deployment of the cartridge 100. In phones equipped with microphones and/or accelerometers, the clicks, sounds, and detectable vibrations transferred to the case 10 through the housing 110 associated with the movement of the safety latch 46, the depression of the button 102, the release of the spring 120, and the engagement of the locking pins 112, 114 with the ports 116, 118 can be detected by the phone, and the emergency notification signals can be generated automatically.

Manufacture of the cases described herein (e.g., the cases 10, 210) can be achieved by separately producing an injection portion having a hollow cavity and safety latch covering the cavity (e.g., the injection portions 40, 240). The injection portion once produced can be welded, melded, or otherwise rigidly adhered to a number of different phone portions that are configured to securely adhere to a personal electronic device.

In some instances, the fluid medicament hypodermically delivered by the auto-injector cartridge 100 is epinephrine, insulin, or calcium, or another fluid medicament suitable for hypodermic injection.

While there has been shown and described in some embodiments of an auto-injection device, it will be appreciated that many changes and modifications can be made therein without, however, departing from the essential spirit thereof. Thus, the disclosure is not limited to the particular embodiments disclosed herein, for it can be realized that various size and/or shapes of the housing of the case, the sheath, the cartridge, and/or the features of the injection device can be readily modified to take on a different form factor for the purposes of the present disclosure. The terminology used herein is for the purpose of describing particular embodiments only, and is not intended to limit the scope of the present invention, which is defined solely by the claims.

The singular terms "a," "an," and "the" include plural referents unless context clearly indicates otherwise. Similarly, the word "or" is intended to include "and" unless the context clearly indicates otherwise.

Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

All numbers expressing quantities used herein should be understood as modified in all instances by the term "about." The term "about" or "approximately" when used in connection with percentages may mean±1%.

Various changes and modifications to the disclosed embodiments, which will be apparent to those of skill in the art, may be made without departing from the spirit and scope of the present invention. Further, all patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

What is claimed is:

1. A hypodermic injection device, comprising: an enclosure having an internal cavity, the enclosure including a safety cover preventing access to a button while the safety cover is in a closed position; a cartridge situated within the cavity and configured to be slidably displaced within the cavity, the cartridge including: a housing, a reservoir housing at least one dose of a fluid medicament; a cannula having a first end configured for hypodermic injection, a second end opposite the first end, and an inner channel in fluid connection with the reservoir, the inner channel terminating proximate the first end of the cannula; a spring-loaded plunger configured to urge the fluid medicament through the inner channel of the cannula responsive to release of a safety catch preventing actuation of the spring-loaded plunger; a resilient sheath covering the first end of the cannula so as to maintain the cannula in a sterile condition; and one or more locking pins, biased outwardly from the cartridge and adapted to be received by one or more complementary ports so as to secure the cartridge in the enclosure and thereby prevent at least a portion of the cartridge including the cannula from sliding with respect to the cavity; a release arm situated to release the safety catch responsive to the resilient sheath being urged toward the housing, and wherein the cartridge is configured to be urged from a first position, where the cannula is situated entirely within the internal cavity of the enclosure, to a second position, where the first end of the cannula extends from the internal cavity to an exterior of the enclosure, the cartridge being urged to the second position in response to the depression of the button covered by the safety cover.

2. The hypodermic injection device according to claim 1, wherein the button is mechanically linked to the cartridge within the enclosure such that at least a portion of the cartridge including the cannula is slidably displaced through the cavity in response to the depression of the button.

3. The hypodermic injection device according to claim 1, wherein the one or more locking pins and the one or more complementary ports are arranged such that the first end of the cannula is extended from the enclosure when the one or more locking pins is received within the one or more complementary ports.

4. The hypodermic injection device according to claim 1, wherein the one or more ports are included in the cartridge and receive the one or more complementary locking pins extending from internal walls of the cavity and biased toward an interior of the cavity.

5. The hypodermic injection device according to claim 1, wherein the cartridge further includes a signal generator for generating a notification signal, the signal generator being configured to send the notification signal in response to the cartridge being secured in the second position.

6. The hypodermic injection device according to claim 1, wherein the fluid medicament is at least one of epinephrine, insulin, or calcium.

7. The hypodermic injection device according to claim 1, wherein the release arm forms at least a portion of a sub-assembly surrounding the cannula and situated to be co-moving with the resilient sheath such that the release arm is urged to release the safety catch responsive to the sheath being urged toward the cannula.

8. The hypodermic injection device according to claim 1, wherein the resilient sheath includes an integrated fluid impermeable barrier that is punctured by the first end of the cannula responsive to the sheath being urged toward the housing while the cannula is secured in the second position.

9. The hypodermic injection device according to claim 1, wherein said locking pins secure the cartridge in the enclosure and thereby securing at least a portion of the cartridge including the cannula with respect to the cavity while the cannula extends to the exterior of the enclosure.

10. The hypodermic injection device according to claim 1, wherein the enclosure is attached to a portable electronic device.

11. The hypodermic injection device according to claim 10, wherein the cartridge further includes a signal generator for generating a notification signal to be received by the portable electronic device securely attached to the enclosure, the signal generator being configured to send the notification signal in response to the cartridge being secured in the second position.

12. The hypodermic injection device according to claim 10, wherein the enclosure further includes a mating interface defining at least one external face of the enclosure, the mating interface configured to securely attach to the portable electronic device.

13. The hypodermic injection device according to claim 10, wherein the portable electronic device is at least one of a cellular telephone, a digital music player, or a personal digital assistant.

14. A cartridge configured to be slidably mounted within a cavity of an enclosure configured to be securely attached to a portable electronic device, the cartridge comprising: a housing, a reservoir housing at least one dose of a fluid medicament; a cannula having a first end configured for hypodermic injection, a second end opposite the first end, and an inner channel in fluid connection with the reservoir, the inner channel terminating proximate the first end of the cannula; a spring-loaded plunger configured to urge the fluid medicament through the inner channel of the cannula responsive to release of a safety catch preventing actuation of the spring-loaded plunger; a resilient sheath covering the first end of the cannula so as to maintain the cannula in a sterile condition; one or more locking pins biased outwardly from the cartridge and configured to be received by one or more complementary ports so as to secure the cartridge in the enclosure and thereby prevent at least a portion of the cartridge including the cannula from sliding within the cavity; and a release arm situated to release the safety catch responsive to the resilient sheath being urged toward the housing.

15. The cartridge according to claim 14, wherein the release arm is at least a portion of an assembly slidably connected to the cartridge, the assembly being rigidly connected to the sheath.

16. The cartridge according to claim 14, wherein the one or more locking pins and the one or more complementary ports are arranged such that the first end of the cannula is extended from the enclosure when the one or more locking pins is received within the one or more complementary ports.

17. The cartridge according to claim 14, wherein the cartridge further includes a signal generator for generating a notification signal to be received by the portable electronic device securely attached to the enclosure, the signal generator being configured to send the notification signal in response to the one or more locking pins being received within the one or more complementary ports.

18. The cartridge according to claim 14, wherein the cartridge further includes a signal generator for generating a notification signal to be received by the portable electronic device securely attached to the enclosure, the signal generator being configured to send the notification signal in response to the one or more ports receiving the one or more complementary locking pins.

19. The cartridge according to claim 14, wherein the release arm forms at least a portion of a sub-assembly surrounding the cannula and situated to be rigidly mechanically linked to the resilient sheath such that the release arm is urged to release the safety catch responsive to the sheath being urged toward the cannula.

20. The cartridge according to claim 14, wherein the resilient sheath includes an integrated fluid impermeable barrier that is punctured by the first end of the cannula responsive to the sheath being urged toward the housing while the cannula is secured with respect to the enclosure such that the first end of the cannula extends from the enclosure.

21. A hypodermic injection device, comprising: an enclosure having an internal cavity, the enclosure including a safety cover preventing access to a button while the safety cover is in a closed position; a cartridge situated within the cavity and configured to be slidably displaced within the cavity, the cartridge including: a housing, a reservoir housing at least one dose of a fluid medicament; a cannula having a first end configured for hypodermic injection, a second end opposite the first end, and an inner channel in fluid connection with the reservoir, the inner channel terminating proximate the first end of the cannula; a spring-loaded plunger configured to urge the fluid medicament through the inner channel of the cannula responsive to release of a safety catch preventing actuation of the spring-loaded plunger; a resilient sheath covering the first end of the cannula so as to maintain the cannula in a sterile condition; and a release arm situated to release the safety catch responsive to the resilient sheath being urged toward the housing, wherein the release arm forms at least a portion of a sub-assembly surrounding the cannula and situated to be co-moving with the resilient sheath such that the release arm is urged to release the safety catch responsive to the sheath being urged toward the housing, and wherein the cartridge is configured to be urged from a first position, where the cannula is situated entirely within the internal cavity of the enclosure, to a second position, where the first end of the cannula extends from the internal cavity to an exterior of the enclosure, the cartridge being urged to the second position in response to the depression of the button covered by the safety cover.

\* \* \* \* \*